United States Patent [19]

Kamen

[11] Patent Number: 4,778,450
[45] Date of Patent: * Oct. 18, 1988

[54] FLUID FLOW CONTROL SYSTEM

[75] Inventor: Dean L. Kamen, Bedford, N.H.

[73] Assignee: Baxter Travenol Laboratories, Inc., Deerfield, Ill.

[*] Notice: The portion of the term of this patent subsequent to Oct. 25, 2000 has been disclaimed.

[21] Appl. No.: 871,714

[22] Filed: Jun. 6, 1986

Related U.S. Application Data

[60] Continuation-in-part of Ser. No. 542,982, Oct. 18, 1983, Pat. No. 4,600,401, which is a division of Ser. No. 254,304, Apr. 15, 1981, Pat. No. 4,411,649, which is a continuation-in-part of Ser. No. 56,871, Jul. 12, 1979, abandoned.

[51] Int. Cl.⁴ .............................................. A61M 5/00
[52] U.S. Cl. ............................. 604/65; 128/DIG. 13; 222/58
[58] Field of Search ............... 128/DIG. 13; 604/65, 604/67, 246, 247, 248, 249, 250; 222/58, 59

[56] References Cited

U.S. PATENT DOCUMENTS

| | | | |
|---|---|---|---|
| 3,329,311 | 7/1967 | Goff et al. | 222/58 |
| 3,481,509 | 12/1969 | Marhauer | 222/58 |
| 3,908,652 | 9/1975 | Weissinger | 604/65 |
| 4,018,362 | 4/1977 | Ubaud | 604/65 |
| 4,029,094 | 6/1977 | Winicki | 128/DIG. 13 |
| 4,098,274 | 7/1978 | Ebling et al. | 604/65 |
| 4,137,915 | 2/1979 | Kamen | 128/DIG. 13 |
| 4,211,340 | 7/1980 | Szakasits | 222/58 |
| 4,300,552 | 11/1982 | Cannon | 604/65 |
| 4,411,649 | 10/1983 | Kamen | 604/65 |
| 4,432,468 | 2/1984 | Siff et al. | 604/65 |
| 4,457,750 | 7/1984 | Hill | 604/65 |
| 4,496,351 | 1/1985 | Hillel et al. | 604/65 |
| 4,507,112 | 3/1985 | Hillel et al. | 604/65 |
| 4,563,173 | 1/1986 | Ledley | 128/DIG. 13 |
| 4,600,401 | 7/1986 | Kamen | 604/65 |
| 4,604,034 | 8/1986 | Wheeldendel | 604/65 |

Primary Examiner—Edward M. Coven
Assistant Examiner—K. M. Reichle
Attorney, Agent, or Firm—Bruce D. Sunstein; Kay H. Pierce; Paul C. Flattery

[57] ABSTRACT

In a fluid flow control system a weight comparator compares the weight of fluid in a reservoir with a weight reference that is programmed to decrease at a desired rate. A fluid flow comparator compares the actual fluid flow rate with a programmed fluid flow rate and operates directly on a flow controller to control fluid flow in the system. The weight comparator operates indirectly on the flow controller by recurringly updating the programmed fluid flow rate so that flow is controlled on a current basis by the fluid flow comparator and on a long-term basis by the weight comparator.

4 Claims, 2 Drawing Sheets

FLUID FLOW CONTROL SYSTEM

This is a continuation-in-part of co-pending application Ser. No. 542,982, filed on Oct. 18, 1983 now U.S. Pat. No. 4,600,401 which is a division of Ser. No. 254,304, filed on Apr. 15, 1981, now U.S. Pat. No. 4,411,649 which is a continuation-in-part of application Ser. No. 056,871, filed on July 12, 1979, now abandoned. Both applications are hereby incorporated by reference.

DESCRIPTION

Technical Field

The present invention relates generally to fluid flow control systems, particularly those used to control the draining of fluid from a reservoir intravenously into a patient.

Background of the Invention

Intravenous fluid control systems are well known in the prior art. The most primitive devices are simply clamps, inserted in physical contact with the fluid line, which are manually adjusted to accomplish the desired flow rate. The invention described in my U.S. Pat. No. 4,137,915 utilizes an electro-mechanical system including an electrically operated clamp, a switch in series with the clamp, and a motor-driven screw and spring arrangement to permit the reservoir to decrease in weight at a rate dependent on the motor speed. Such a system, though a significant advance in the art, requires many moving parts and is limited in accuracy by sensitivity of the switch and mechanical friction and hysteresis.

DISCLOSURE OF INVENTION

The invention provides a weight detector, for generating a weight measurement signal that is indicative of the weight of fluid in the reservoir; an adjustable reference generator for generating a weight reference signal that is indicative of the desired rate of decrease in weight of the fluid in the reservoir; and a comparator that produces an output indicative of the dissimilarity between the weight measurement and the weight reference signals. Some embodiments utilize a flow controller, operative upon the fluid line from the reservoir to the patient, that has an input connected so as to receive a signal related to the comparator's output.

In a preferred embodiment, the invention includes a drop counter placed in the line of flow from the reservoir. The drop counter produces an actual drop rate signal. There is also provided a device that generates a programmed drop rate signal. The programmed drop rate signal is modified by the previously described comparator's output to produce a corrected drop rate signal. The actual and the corrected drop rate signals are directed to a second comparator that operates on the flow controller.

DESCRIPTION OF SPECIFIC EMBODIMENTS

Figure 1:
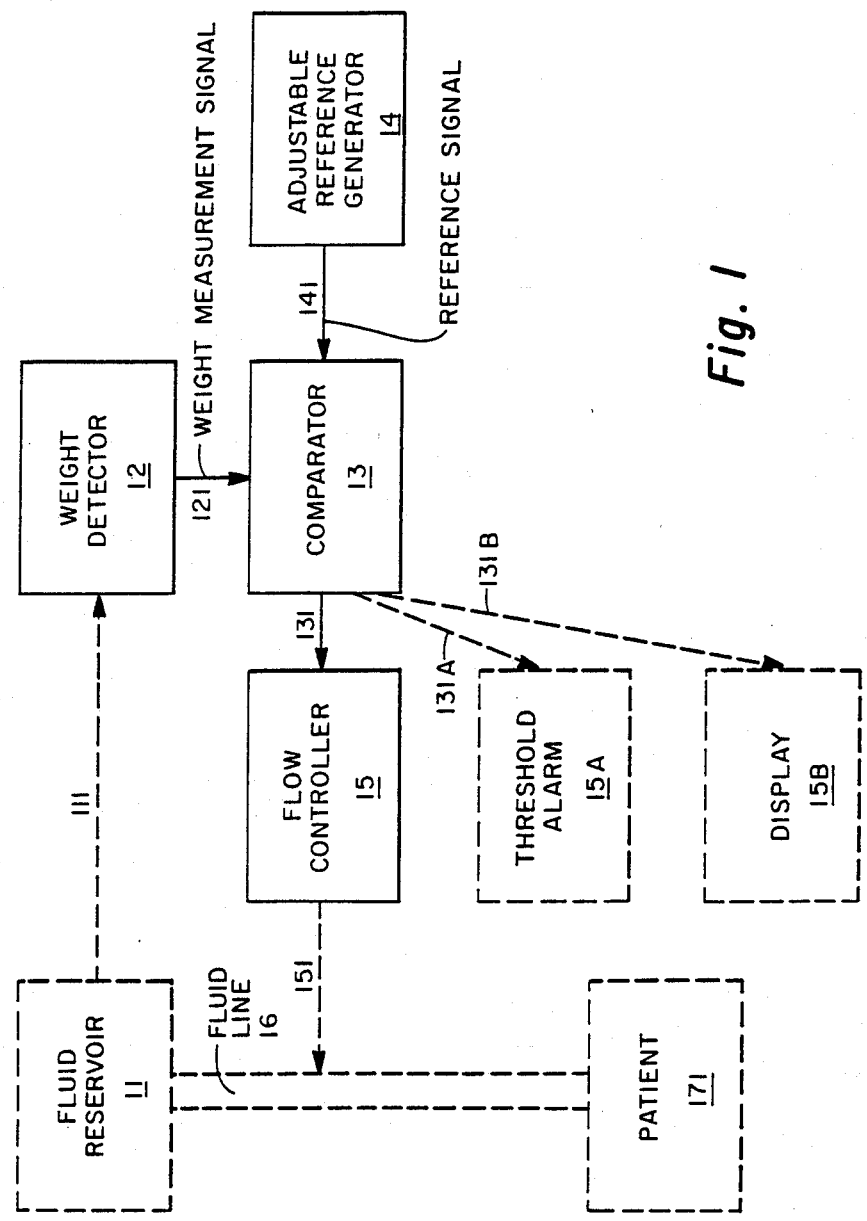
FIG. 1 is a block diagram of a basic fluid flow control system in accordance with the present invention.

Referring to FIG. 1, there is shown a basic embodiment of the invention. The invention operates on a fluid line 16 that is placed between a fluid reservoir 11 and the patient 171. Weight of the fluid reservoir is monitored by weight detector 12. The mechanical relation between the reservoir 11 and the weight detector 12 is indicated by arrow 111. Weight detector 12 may be any electronic device for producing an output as a function of weight of the reservoir, and may, for example, be a strain gauge. As fluid leaves the fluid reservoir 11, the reservoir decreases in weight, and the weight measurement signal, which is an output of weight detector 12 appearing on line 121, will be appropriately modified over time with decrease of the weight in the fluid reservoir. Reference generator 14 provides a reference signal over line 141 that is indicative, at any given time, of the desired value of the weight measurement signal.

The weight measurement and reference signals may be either analong or digital. If such signals are analog, it may be desirable to utilize direct current signals having magnitudes proportional respectively to the measured and desired weights of the fluid reservoir. The reference signals may be programmed to indicate a weight decrease of the fluid reservoir at any desired rate. For example, it may be desired to have the flow in the reservoir cease except during a specified one-hour interval each day. In such a case, for example, the reference signal would then be kept at a constant level except during the specified hour, at which time the reference signal would decrease in accordance with the flow rate desired over that hour; thereafter, the reference signal would again be constant until the next day. The adjustable reference generator may incorporate microprocessors, in accordance with techniques well known in the prior art, to produce such a reference signal.

Still referring to FIG. 1, the reference signal and weight measurement signal are both separate inputs to the comparator 13, which produces an output indicative of the dissimilarity (for example the algebraic difference) between the two signals. The output appears on line 131. It will be appaent, of course, if the weight measurement and reference signals are digital, that the comparator must also be digital. Alternatively, the reference generator 14 may utilize digital processing circuits and appropriate digital-to-analog converters so that the weight measurement and reference signals are both analog. The dissimilarity indicated by the comparator can be a simple "go, no-go" output, an algebraic difference, a phase angle change, or any signal suitable for affecting the flow controller 15. In any event, the comparator output 131 is used to operate on flow controller 15. The controller may be a simple solenoid-operated clamp, which is either opened or closed (and therefore cycling off and on as many times as necessary to produce the appropriate average flow rate), or it may be continuously adjustable to produce a more precisely controlled flow. Because the rate of decrease of the fluid reservoir may be monitored continuously by rate detector 12, the flow controller need only have the means for operating over a suitable range of flow so as to permit operating of the system. Thus, the flow controller is not limited to a clamp-type device, but may take other forms, such as a pump with a continuously variable rate of operation.

As an alternative, or even in addition, to the flow controller 15 may be a threshold alarm 15A. The alarm emits a detectable signal (such as an audible noise) whenever the signal over line 131A from the comparator 13 is indicative of a difference, between actual cumulative flow (as represented by the weight measurement signal) and desired cumulative flow (as represented by the weight reference signal), that is outside some predetermined set of limits. Also connected to the comparator 13 may be a display 15B for displaying the amount and/or algebraic sign of the foregoing difference. Thus, if the threshold alarm 15 indicates that the cumulative flow is too great or too small, the flow can be adjusted appropriately. When used in conjunction with the flow controller 15, the threshold alarm will given warning (i) whenever the flow controller 15 is not functioning properly, or (ii) whenever the fluid reservoir 11 is empty, or (iii) generally whenever blockage or other circumstances undesirably inhibits or increases flow. When used without the flow controller 15, the threshold alarm will give warning under comparable conditions, and alert the user to any circumstance when a manual flow control should be adjusted. In correcting circumstances giving rise to the activation of alarm 15, the user may utilize the display 15B.

Figure 2:
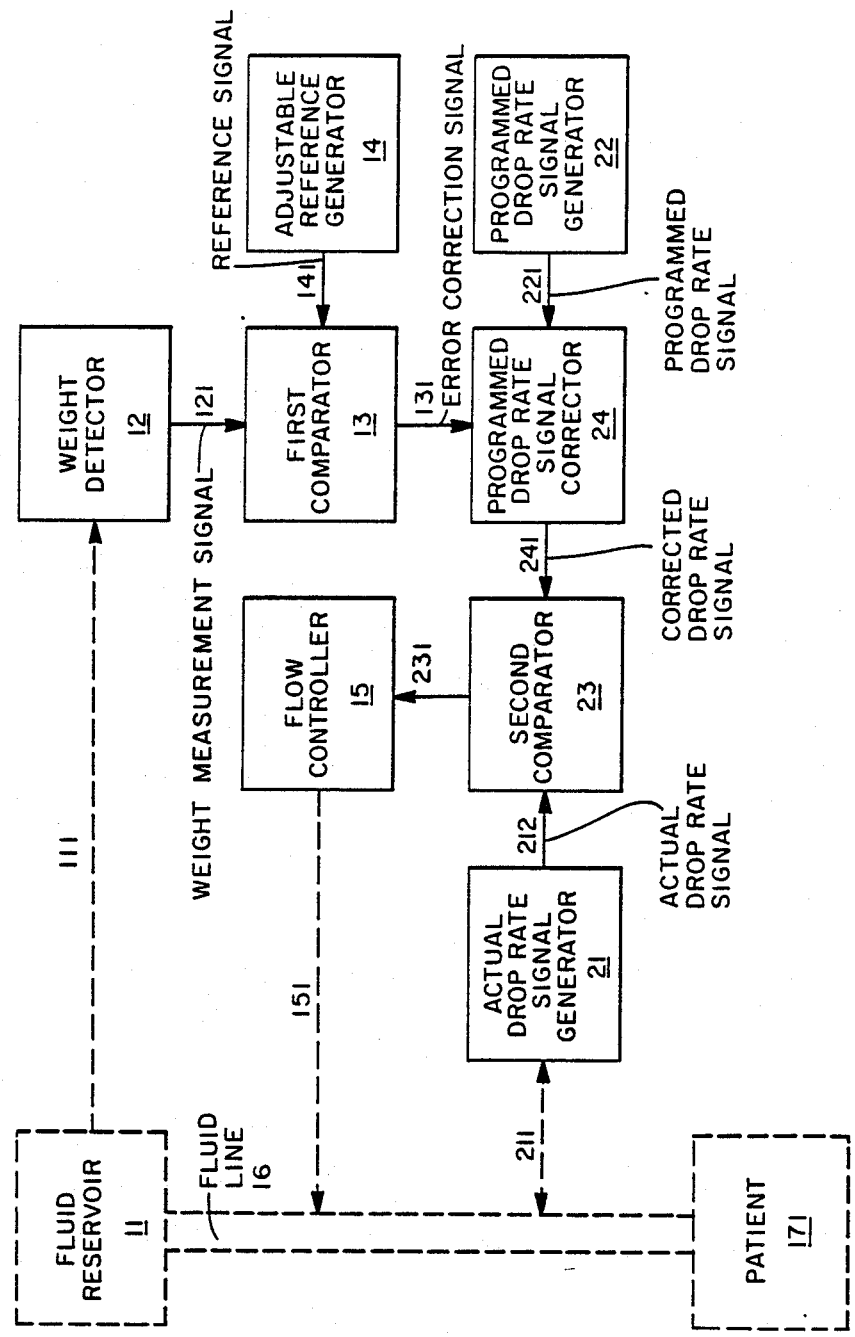
FIG. 2 is a block diagram of a more sophisticated emodiment of the present invention, where a drop counter is utilized.

Referring now to FIG. 2, there is shown a more sophisticated embodiment of the present invention. This embodiment is generally similar to that described with reference to FIG. 1, except that "drop rate" circuitry is used to provide better instantaneous control of flow. There is inserted, in the fluid line 16, an actual drop rate signal generator 21. This signal generator 21 has an output on line 212 that is indicative of the actual drop rate that is measured. This output is called the "actual drop rate signal." The programmed drop rate signal generator 22 has an output on line 221 that is called the "programmed drop rate signal." This signal is an input to the programmed drop rate signal corrector 24, which in turn provides an output, over line 241, called the "corrected drop rate signal." The dissimilarity between the actual and corrected drop rate signals, which are both inputs to the second comparator 23, appears as a function of the output of the second comparator on line 231. This output is used to control the flow controller 15.

Still referring to FIG. 2, initially the programmed drop rate signal, through corrector 24 and second comparator 23, causes operation of the flow controller 15 until the actual drop rate signal is approximately matched by the programmed drop rate signal. However, adjustable reference generator 14 in combination with detector 12, in the manner discussed in connection with FIG. 1, causes an output of the first comparator 13 on line 131 to be indicative of the difference between the actual flow through fluid line 16 and the desired flow. This output is called the error correction signal, and is used as an input to the programmed drop rate signal corrector 24, to produce a corrected drop rate signal on line 241. In this manner, flow through the system on a drop-by-drop basis is controllable by the actual drop rate signal generator 21, the second comparator 23, and the programmed drop rate signal generator 22 and corrector 24; whereas the time-averaged flow is also being monitored by the weight detector 12, the first comparator 13, and the adjustable reference generator 14, which, in combination, keep the instantaneous flow under control so as to produce the appropriate time-averaged behavior of the system.

It will be clear that although the present embodiment contemplates the use of "drop rate" circuitry to provide better instantaneous control of flow, it would be equally within the scope of the invention to use "pump rate" circuitry which would involve the insertion into the fluid line of a pump and an actual pump rate signal generator. Pumps of various types for use with intravenous flow lines are well known in the art; the actual pump rate signal generator would be pegged to the rate of fluid known to be displaced by the pump. As in the embodiment shown in FIG. 2, the pump rate embodiment would include an output from the actual pump rate signal generator which would be compared with the output from a programmed pump rate signal generator, which would be corrected by an error correction signal generated by an adjustable reference generator, and so forth.

As used in the claims, the "current fluid flow rate" term includes reference to the actual drop rate or the actual pump rate or to any equivalent; the term "programmed flow rate" includes reference to the programmed drop rate or the programmed pump rate or to any equivalent; and the term "flow controller means" includes a controllable valve or controllable pump.

For many applications, the output of the programmed drop rate signal generator 22 which is produced when the system is first turned on, may be somewhat arbitrary, because within a short time the appropriate error correction signal will appear over line 131, and cause a corrected drop rate signal to appear on line 241. As in the case of generator 14 (as discussed in connection with FIG. 1), the programmed drop rate signal generator 22 and corrector 24 can be made in accordance with designs well known in the prior art. One possible embodiment would be a microprocessor-controlled device that includes a digital-to-analog convertor to permit the output of an analog signal on line 241. Alternatively, the circuitry could be conventional analog circuitry. If more precision is desired when the system is first turned on, the programmed drop rate signal generator 22 can be provided with suitable adjustment to provide a desired initial instantaneous flow rate. The interaction of the drop rate flow measurement signal generator 21 with the fluid line 16 is indicated schematically by double arrow 211.

It will be clear that the error correction signal need not necessarily be provided to the corrector 24 on a continuous basis, so long as drift of the system's accuracy is kept within desired limits; the corrector may be designed to provide a corrected drop rate signal of one specification until a new error correction signal requires the corrector 24 to produce a signal. Thus the weight measurement and reference signals need not necessarily be continuous.

Similarly, the corrected and actual drop rate signals themselves need not necessarily be continuous, since the second comparator 23 and the flow controller 15 may be designed to operate with signals provided at a given clock frequency. Generally, it is desirable to have the clock rate or sample rate of the drop rate circuitry be sufficiently high; otherwise the drop rate circuitry may not significantly improve on the embodiment shown in FIG. 1.

What is claimed is:

1. A system for controlling in a desired manner the flow of fluid in a line from a reservoir to a patient, the system comprising:
   weight measurement means for mesuring the weight of fluid in the reservoir and producing a weight measurement signal;

weight reference means for providing a weight reference signal that is programmed to decrease at a desired rate;

weight comparison means for comparing the weight measurement signal with the weight reference signal and for producing an output indicative of the dissimilarity between the two signals;

flow controller means for regulating the fluid flow in the line from the reservoir;

fluid flow measurement means, placed in the line of flow from the reservoir, for determining the fluid flow rate and producing an actual fluid flow rate signal;

programmed fluid flow rate means, in communication with the output of the weight comparison means, for providing a programmed fluid flow rate signal that is recurringly updated on the basis of the output of the weight comparison means;

fluid flow comparison means for comparing the actual fluid flow rate signal with the programmed fluid flow rate signal, and for producing an output indicative of the dissimilarity between the two signals, the fluid flow comparison means being directly operative on the flow controller means;

whereby the fluid flow rate is directly controlled by the dissimilarity between the actual fluid flow rate and the programmed fluid flow rate and the programmed fluid flow rate signal is recurringly updated by the weight comparison means, so that the flow rate of fluid is ultimately controlled by the weight reference means.

2. A system according to claim 1, wherein the flow controller means is a pump.

3. A system according to claim 1, wherein said weight measurement means is an electrical means, said weight reference means is an electrical means, and fluid flow measurement means is an electrical means.

4. A system according to claim 3, wherein the flow controller means is a pump.

* * * * *